United States Patent
Zhang et al.

(10) Patent No.: US 8,476,500 B2
(45) Date of Patent: Jul. 2, 2013

(54) INBRED TETRAPLOID WATERMELON LINE 4XASSS4

(75) Inventors: Xingping Zhang, Woodland, CA (US); James Brusca, Woodland, CA (US)

(73) Assignee: Syngenta Participations AG, Basel (CH)

(*) Notice: Subject to any disclaimer, the term of this patent is extended or adjusted under 35 U.S.C. 154(b) by 272 days.

(21) Appl. No.: 13/036,130

(22) Filed: Feb. 28, 2011

(65) Prior Publication Data

US 2012/0222152 A1    Aug. 30, 2012

(51) Int. Cl.
  *A01H 1/00* (2006.01)
  *A01H 5/00* (2006.01)
  *A01H 5/10* (2006.01)

(52) U.S. Cl.
  USPC .......................................... 800/308; 800/260

(58) Field of Classification Search
  USPC ........................................................ 800/308
  See application file for complete search history.

(56) References Cited

U.S. PATENT DOCUMENTS 7,667,101 B2 * 2/2010 Barham ..................... 800/308

* cited by examiner

*Primary Examiner* — Anne Kubelik
(74) *Attorney, Agent, or Firm* — Karen Magri; Syngenta Participations AG

(57) ABSTRACT

A tetraploid watermelon inbred 4XASSS4 is disclosed. The invention relates to the seeds and plants of tetraploid watermelon inbred 4XASSS4, the methods of propagating the tetraploid inbred 4XASSS4 through seeds and tissue culture. The invention also relates to methods of producing the triploid seedless watermelon seeds and plants by crossing inbred 4XASSS4 with diploid watermelon inbreds, and to the triploid plants produced therefrom. The invention further relates to the methods of developing new tetraploid lines by using tetraploid inbred 4XASSS4 as breeding material, and to tetraploid watermelon seeds and plants produced therefrom.

15 Claims, No Drawings

INBRED TETRAPLOID WATERMELON LINE 4XASSS4

FIELD OF THE INVENTION

This invention is in the field of watermelon breeding, specifically relating to a tetraploid watermelon used to produce triploid seeds and plants for production of a seedless watermelon fruit.

BACKGROUND OF THE INVENTION

This invention relates to a new and unique inbred tetraploid watermelon line, designated 4XASSS4.

Watermelon is an important horticultural crop that accounts for 2% of the world area devoted to vegetable crops. There were 3,810,535 Ha of watermelon grown in the world and 51,110 Ha of watermelons grown in the United States in 2009. Asia is by far the most important watermelon production site with 78% of the world area and 83.4% of the world production of 100,687,056 metric tones (FAOSTAT|© FAO Statistics Division 2011|20 Feb. 2011; http://faostat.fao.org/site/291/default.aspx). The estimated annual world watermelon value exceeded $7.6 billion when using the United States average price for 1995-1997. Watermelon is grown in forty-four states in the USA, with Florida, Georgia, California, and Texas, having long warm growing seasons, being the major producing states. In the U.S., watermelon production has increased from 1.2 M tons in 1980 to 3.8 M tons in 2009, with an annual farm value of $470 million (U.S. Department of Agriculture, Agricultural Statistics, 2009). In recent years, there has been an increase in consumer demand for seedless watermelons and production of seedless watermelon has increased significantly. Today, over 80% of the watermelons produced in the United States are triploid seedless watermelons (U.S. National Watermelon Promotion Board; www.watermelon.org). Seedless watermelon receives well above the average price for seeded watermelons in the market. Triploid seedless watermelon also produces higher yields than the diploid seeded watermelons.

Triploid seedless watermelon is a true F1 hybrid between a tetraploid watermelon, as the female parent, and a diploid watermelon, as the male parent (Kihara, H. 1951, *Triploid Watermelons*, Proceedings of American Society for Horticultural Science, 58:217-230). Regular watermelons, the seeded diploid watermelons, have 22 chromosomes (2N=2X=22) in their somatic cells. The tetraploid watermelons have 44 chromosomes (2N=4X=44) in their somatic cells. When female flowers of tetraploid plants are crossed pollinated by the male flowers of normal diploid plants, the seeds produced in the fruit of tetraploid plants are triploid seeds. Triploid seeds produce triploid plants. When the triploids plants are grown with the normal diploid plants in the same field, the triploid plants produce fruits that are seedless. The seedless condition in triploid watermelon is the result of the presence of three homologous sets of chromosome per somatic cell rather than the usual two. Cells with three sets of homologous chromosomes are said to be triploid and are designated as 3X. The triploid seedless watermelons have 33 chromosomes (2N=3X=33) in their somatic cells. The inability of the triploid zygote to produce normal viable gametes (pollen and egg cells) causes the absence of seeds in triploid fruits. Typically, seedless watermelons contain small edible white ovules, similar to those in immature cucumbers.

Triploid seedless watermelons have been commercially grown in the United States since the late 1980's. The popularity of seedless watermelon has increased since its commercial introduction in the United States. Most of the watermelons produced in California in 2010 were triploid seedless watermelons. Triploid varieties produce higher yields than the diploid seeded varieties, due to more fruit per plant and longer harvest period. The triploid seedless watermelon receives premium prices because of the high quality flesh virtually free of seeds.

SUMMARY OF THE INVENTION

The invention comprises a novel inbred tetraploid watermelon, designated 4XASSS4. The present invention includes the seeds of the inbred tetraploid watermelon line 4XASSS4, methods of producing hybrid triploid watermelon seeds using 4XASSS4, methods of producing seeds having all the genetics of 4XASSS4, and methods of developing new inbred tetraploid lines using 4XASSS4. This invention further includes triploid hybrid watermelon seeds and plants produced by crossing 4XASSS4 with a diploid watermelon line.

DETAILED DESCRIPTION OF THE INVENTION

In commercial production of triploid watermelon seed, tetraploid and diploid parental lines are planted in the same field. Cross-pollination between the tetraploid line, the female parental line, and the diploid line, the male parental line, are accomplished by either hand or bee pollination. Triploid watermelon seeds are produced only in melons of tetraploid plants that are fertilized with pollen of diploid plants. All commercially grown seeded watermelons are diploid; therefore, there are many diploid lines for use as diploid parents. The major limitation to development of seedless watermelon varieties lies in the availability of useful elite tetraploid parental lines.

Tetraploid watermelon lines are developed by doubling the chromosomes of regular diploid watermelon lines. Chromosome doubling was first accomplished with the toxic alkaloid colchicine by applying colchicine to the growing point of new emerged watermelon seedlings. Tissue culture methods have also been developed by Zhang, X. P., B. B. Rhodes, H. T. Skorupska, W. C. Bridges, 1995, *Generating Tetraploid Watermelon Using Colchicine in Vitro*, G. Lester & J. Dunlap et al. (eds.), Cucurbitaceae' 94: 134-139. Dinitroanilines have been used to double chromosome numbers, and their effectiveness has previously been compared with crops other than watermelon. Li et al (Li, Ying, J. F. Whitesides, B. Rhodes, 1999, *In vitro generation of tetraploid watermelon with two different dinitroanilines and colchicines*, Cucurbit Genetics Cooperative Rpt 22:38-40) compared in vitro chromosome doubling effectiveness using colchicine and the dinitroanilines, ethalfluralin (N-ethyl-N-2-methyl-2-propenyl)-2,6-dinitro-4-(trifluoromethyl)benzanine), and oryzalin (3,5-dinitro-N4, N4-dipropylsulfanilamide) and concluded that either ethalfluralin or oryzalin was preferable to colchicine.

Several treatment methods are used to induce tetraploids from diploids using the chemicals mentioned above. One method is to treat the seed before sowing. The seed are soaked in clean water for 5-6 hrs and then the seed are soaked in either colchicine solution (0.2%) or dinitroanilines (e.g. 35 μM oryzalin) for 24 hrs. The seed are briefly rinsed before sowing. Dry seed can also be directly soaked in the chemical solution without pre-soaking in the water. This treatment is simple to do and is a good method to use if one has no restriction of seed supply. The treatment usually reduces the germination and emergence. The second method is to treat the new emerged seedling. The diploid inbreds are sown in greenhouse in seedling flats. The soil temperature is kept at 29-31° C. for rapid and uniform germination. One drop of colchicine (0.1%) or dinitroanilines (e.g. 35 µM oryzalin) solution is added to the shoot apex between the cotyledons as soon as the seedling has emerged from soil. The colchicine solution is applied to the growing point in the morning or evening for three consecutive days. We get good chromosome doubling from one application of oryzalin. Another method is to treat the shoot apex of germinated seed after which the germinated seed is planted into soil. The seeds are germinated in an incubator at 30° C. When the radicals are about 2 cm long, the portion above the hypocotyls of germinated seeds is immersed upside down into colchicine (0.1%) or dinitroaniline solution (35 µM oryzalin) for 10-15 hrs at 30° C. in an incubator. The treatment should be conducted in a high humidity chamber or box to assure that the radicals/roots are not desiccated. The seeds are then washed and planted in the soil. The last two methods, although more tedious to use, usually give better recovery of tetraploid events as the root system is not affected by the treatment.

The next step is to develop tetraploid lines from individual converting events. The selected tetraploid individuals based on morphological expression are self-pollinated and the resulting seeds are planted in the next generation as lines. These lines are again self-pollinated and compared for fertility and horticultural traits. Only the desirable lines are selected if there is difference among these lines. Desirable lines may be bulk harvested if there is no variation within the line and among selected lines. Further seed increases may be conducted in an isolation block. Mass selection may be conducted for this increase in the isolation plot and thereafter. Fertility of the tetraploid may be improved in subsequent generations.

The use of tissue culture to propagate tetraploid watermelon plants is further exemplified in Adelberg, J. W., B. B. Rhodes, *Microprogpogation from zygotic tissue of watermelon*, C. E. Thomas (ed.) Proc. of the Cucurbitaceae 89: *Evaluation and enhancement of cucurbit germplasm*, Charleston S.C., USA; and Zhang et al., *Shoot regeneration from immature cotyledon of watermelon*, Cucurbit Genetics Coop. 17:111-115 (1994).

Crossing two different tetraploids and then going through recombination breeding can also result in new tetraploid lines. A longer breeding period is required to develop a stable tetraploid line using this approach. This is due to the larger number of combinations and the fewer seed that tetraploids produce. However, some breeders make good progress by taking this approach.

Because meiosis is sometimes irregular in autotetraploids, diploids and aneuploids do occur in their offspring. The leaves, flowers and pollen grains of tetraploids are morphologically distinct from diploids (Zhang, X. P., B. B. Rhodes, H. T. Skorupska, W. C. Bridges, 1995, *Generating Tetraploid Watermelon Using Colchicine in Vitro*, G. Lester & J. Dunlap et al. (eds.), Cucurbitaceae' 94: 134-139). Tetraploids also have a different number of chloroplasts in the guard cells (Compton, M. E., D. J. Gray and G. W. Elmstrom. 1996, *Identification of tetraploid regenerants from cotyledons of diploid watermelon cultures in vitro*, Euphytica 87:165-172). These morphological traits can help breeder to eliminate the diploids and aneuploids occurring in the tetraploid population during sexual propagation.

Triploid seeds are currently produced using two methods, the bee-pollination method and the hand-pollination method. In the United States, the bee-pollination method is used to produce triploid watermelon seed. Almost all of the United States triploid watermelon seed production is located in Northern California. The production fields are typically planted in a ratio of 2 rows of tetraploid female line and 1 row of diploid male line. All the male flower buds are manually removed from the female tetraploid plants. This process is known as de-budding. The female flowers are open-pollinated by bees. The fruit set during the de-budding period are marked and harvested for triploid hybrid seed. Male buds are manually removed from tetraploid female vines throughout the pollination season. If a male sterile tetraploid line is available, workers can easily remove the male fertile plants in the tetraploid female row with much less time and efforts. All the fruit set on the male-sterile tetraploid plants can be harvested for hybrid triploid seed. When the marked male-sterile system is used, seed producer can insure that no female off-types exist in the female tetraploid line and the hybrid triploid production field (Zhang, X. P. and B. B. Rhodes, 2000, *Method using male sterility and a marker to produce hybrid seeds and plants; U.S. Pat. No. 6,018,101*).

Hand-pollination is mainly used to produce triploid watermelon seed in areas where isolation is not available and several triploid hybrids are produce in the same field block. Inbred male parent line is sown 7-10 days earlier than inbred female tetraploid parent line. The male parent is usually located outside of the crossing block. Approximately four to ten tetraploid female plants per male plant are planted to insure adequate pollination and achieve high triploid seed yield. The male parent is carefully checked for its uniformity before male flowers are collected. Any off-types that can be recognized based on plant morphology and ovary characteristics are removed. Pollination starts when the second female flowers of the tetraploid female parent are ready to flower. The female flower buds of the tetraploid female parent line are identified and covered with paper cups or small paper bags before they bloom the next morning. Male flowers of the diploid male parent line are collected in the early morning before the visit of bees or other pollination insects to the flowers. The covered female flower buds are then uncovered and pollinated using the collected fresh male flowers. The pollinated female flowers are then re-covered and marked. The open-pollinated fruits on the female parent plants are removed periodically to insure the development of hand-pollinated fruits. Male plants are removed from the field after pollination is complete to insure that only fruit from female parents are harvested.

Inbred 4XASSS4

The development of 4XASSS4 started from a cross between Syngenta tetraploid breeding lines 90-4265 and 90-4228 (PVP No. 200000346). 90-4265 is a selection out of United States Vegetable Labs (USDA) release 'Tetra-4'. 4XASSS4 was developed at Syngenta Seeds' Research Stations in Woodland, Calif., Naples, Fla., and Khon Kaen, Thailand, as a result of traditional recombination breeding. 4XASSS4 is an oval shaped tetraploid watermelon breeding line with an Allsweet stripe and small seed size and resistance to Fusarium wilt race 1 and Anthracnose race 1.

The typical pedigree breeding method was used for the development of 4XASSS4. The breeding goal of 4XASSS4 was to combine the oval fruit shape, Allsweet stripes, nice red flesh, resistance to Fusarium wilt race 1 and Anthracnose race 1 of tetraploid line 90-4228, with the small seed size, good fruit set, firmer flesh texture and high seed number per fruit of 90-4265.

The first cross of the two initial tetraploid lines 90-4265 and 90-4228 was made in the field in the spring of 2004 at Naples, Fla. station of Syngenta Seeds, Inc. The F2 seed were made in the field in the fall 2004 in Naples. The F2 population was screened for resistance to Fon 1 (Fusarium wilt race 1) at the seedling stage and the resistant individuals were grown in the greenhouse in the winter of 2005. Five desirable individuals were selected from F2 generation.

The pedigree selections from generations F3 to F8 were then conducted in the open field in Khon Kaen, Thailand, with periodic Fon 1 disease indexing in the greenhouse in Woodland, Calif. A F9 line with pedigree of (90-4265/90-4228)4-4-1-8-3-2-B-B was advanced to line 4XASSS4 because of its desirable horticultural characteristics and uniform and stable genetics. Three more generations of inbreeding were conducted in the breeding nursery to ensure stability of the line and to increase the amount of breeder seed. Seed of 4XASSS4 at the F12 generation were provided for seed increase in Woodland, Calif. in the summer of 2009 in net-cages with about 1,200 plants. No variant was observed in this line. The seed of 4XASSS4 at F13 generation were produced. No genetic variation is expected in variety 4XASSS4.

Test crosses of triploid hybrids using 4XASSS4 as female parent have been evaluated in California and Florida. Promising triploid hybrids have been selected for multiple location trials. 4XASSS4 is a new, unique and useful elite tetraploid for producing triploid seedless hybrids.

Based on the observations of the large number of plants in the last four generations, the 4XASSS4 tetraploid line is genetically stable and phenotypically uniform. No variants have been observed in the population of 4XASSS4 and no variation is expected in variety 4XASSS4.

The unique characteristics of inbred 4XASSS4 are described as follows:

Compared to the most similar varieties, 90-4228 and 90-426, new watermelon tetraploid variety 4XASSS4 is unique in that it combines the following traits: small seed size (conferred by the Ti gene), resistance to Fusarium wilt race 1 (conferred by the Fo-1 gene), an Allsweet striping pattern, nice red flesh color and oval fruit shape.

Compared to 90-4228, 4XASSS4 has a smaller seed size. This is a qualitative difference in seed size conferred by the Ti gene (Tanaka, T., Wimol, S., and T. Mizutani. 1995. *Inheritance of fruit shape and seed size of watermelon*. J. Japan. Soc. Hort. Sci. 64(3): 543-548) as shown in Table 1. This is the only striped Allsweet type tetraploid having small seed size.

4XASSS4 is also unique in that it has resistance to Fusarium wilt race 1, conferred by the gene Fo-1 (Henderson, W. R., S. F. Jenkins, Jr., and J. O. Rawlings. 1970. *The inheritance of Fusarium wilt resistance in watermelon, Citrillus lanatus* (*Thunb.*) Mansf. J. Amer. Soc. Hort. Sci. 95: 276-282) as the standard pathology test results show in Tables 2 and 3. 90-4265 does not carry the resistance allele at the Fo-1 locus and is susceptible to Fusarium wilt race 1. 90-4228 carries the resistance allele at the Fo-1 locus and is resistant to Fusarium wilt race 1.

4XASSS4 is also resistant to Anthracnose race 1 as shown by pathology test results in Table 4 below.

TABLE 1

Seed size data for 4XASSS4, 90-4228, and 90-4265.

| Variety | Thousand Seed Weight (grams) | Seed length (mm) | Seed width (mm) | Seed thickness (mm) | Ti locus genotype |
|---|---|---|---|---|---|
| 4XASSS4 | 36 | 7 | 5 | 2.5 | TiTiTiTi |
| 90-4265 | 39 | 7.5 | 5.5 | 2.7 | TiTiTiTi |
| 90-4228 | 77 | 10.5 | 7 | 3.3 | titititi |

TABLE 2

Test of Resistance to Fusarium wilt race 1 in 4XASSS4 and controls.

| Variety | Species | Isolate Used | Total Plant Inoculated | R | S | % R | Results |
|---|---|---|---|---|---|---|---|
| 4XASSS4 | Citrullus lanatus var. lanatus | Race 1 (811B) | 68 | 64 | 4 | 94% | Resistant |
| Calhoun Grey | Citrullus lanatus var. lanatus | Race 1 (811B) | 18 | 18 | 0 | 100% | Resistant |
| Black Diamond | Citrullus lanatus var. lanatus | Race 1 (811B) | 15 | 0 | 15 | 0% | Susceptible |

Standard Fusarium wilt resistant test protocol was used for this test. The test was conducted in the pathology greenhouse of Woodland station and was finished in November, 2008. "R"=resistant plants, "S"=susceptible plants. 4XASSS4 is resistant to Fusarium wilt race 1.

TABLE 3

Test of Resistance to Fusarium wilt race 1 in 4XASSS4 and controls.

| Variety | Species | Isolate Used | Total Plant Inoculated | R | S | % R | Results |
|---|---|---|---|---|---|---|---|
| 4XASSS4 | Citrullus lanatus var. lanatus | Race 1 (811B) | 124 | 118 | 6 | 95 | Resistant |
| Calhoun Grey | Citrullus lanatus var. lanatus | Race 1 (811B) | 125 | 121 | 4 | 97 | Resistant |
| Black Diamond | Citrullus lanatus var. lanatus | Race 1 (811B) | 174 | 1 | 173 | 1 | Susceptible |

Standard Fusarium wilt resistant test protocol was used for this test. The test was conducted in the pathology greenhouse of Woodland station and was finished in July, 2010. "R"=resistant plants, "S"=susceptible plants. 4XASSS4 is resistant to Fusarium wilt race 1.

TABLE 4

Test of Resistance to Anthracnose race 1 in 4XASSS4 and controls.

| Variety | Species | Isolate Used | Total Plant Inoculated | R | S | % R | Results |
|---|---|---|---|---|---|---|---|
| 4XASSS4 | Citrullus lanatus var. lanatus | Col1 (6324) | 156 | 153 | 3 | 98 | Resistant |
| Calhoun Grey | Citrullus lanatus var. lanatus | Col1 (6324) | 118 | 0 | 118 | 0 | Resistant |
| Charleston Grey | Citrullus lanatus var. lanatus | Col1 (6324) | 110 | 110 | 0 | 100 | Susceptible |

The standard anthracnose test was used for this test. The test was conducted in the pathology greenhouse of Woodland station and was finished in December, 2009.

Tetraploid watermelon inbred 4XASSS4 can be multiplied through vegetative propagation and sexual propagation. The vegetative propagation can be done preferably via shoot proliferation and then rooting in tissue culture. The detailed methods were described by Zhang et al. (Zhang, X. P., B. B. Rhodes, H. T. Skorupska, W. C. Bridges. 1995. Generating Tetraploid Watermelon Using Colchicine in Vitro. G. Lester & J. Dunlap et al. (eds.), Cucurbitaceae' 94: 134-139). This method is briefly described as follows: A) Collect shoot-tips and axillary buds from greenhouse, field or laboratory grown plants of 4XASSS4. Rinse the shoot-tips and axillary buds under tape water for 30 minutes to an hour. Sterilize the shoot tips and axillary buds in 10% of household bleach for 8-10 minutes. Rinse the shoot-tips and axillary buds three times in sterilized distilled water. B) Culture the shoot-tips and axillary buds on Murashige and Skoog (MS) medium with 10 µM BA for shoot proliferation. Make a subculture every 3-4 weeks. C) Root the proliferated shoot buds on MS medium with 5-10 µM IBA for about 2 weeks. D) Acclimatize the rooted plantlets in a temperature and humidity controlled greenhouse. E) Grow the micropropagated plants in an isolation plot and harvest the seed from these plants.

Tetraploid watermelons are usually sexually propagated through seed. We have successfully propagated inbred 4XASSS4 in the greenhouse, in a net covered cage, and in the open fields. The seed increase field should be isolated from any other watermelon by at least 1.5 KM, if the seed increase is conducted in the open field. Good pest management and cultural practices should be implemented. Higher (20-30% higher than those used for commercial hybrid fruit production) levels of phosphate and potassium fertilize are beneficial for producing high seed yield and good seed quality. Calcium is supplemented for the fields low in calcium to minimize the fruit loss due to fruit splitting. Beehives are placed in the seed production fields to insure good pollination, the key biological event for seed production. Fruit is preferably harvested before fruit split and deterioration. The harvested fruit is then stored under room temperature for a period of time before extracting seed from fruit, to allow further embryo development and seed maturation in the fruit. The seed, after being extracted from the flesh, is thoroughly washed and quickly dried using a forced-air dryer to best maintain the seed viability.

The primary use of tetraploid watermelon is to make triploid hybrid watermelon seeds and plants that produce seedless fruit. The tetraploid line is used as female parent to cross with the diploid watermelon lines, the male parent lines. The creation of a desirable triploid hybrid heavily relies on the performance, especially seed producibility, and the combining ability of the tetraploid parent.

Several methods can be used to produce triploid seeds from inbred 4XASSS4, once the proper combination is determined. Two commonly used methods are described here. Variations to these methods can be made according to actual production situation.

Hand-Pollination Method

This is the most often used method for producing triploid seed from 4XASSS4. The inbred tetraploid female parent 4XASSS4 and the inbred diploid male parent line are planted in the same field. The inbred male parent is planted 7-10 day earlier than the female parent 4XASSS4 to insure adequate pollen supply at the pollination time. The male parent and female parent 4XASSS4 are planted in the ratio of 1 male parent to 4-10 female parents. The diploid male parent may be planted at the top of the field for efficient male flower collection during pollination. Pollination is started when the second female flower on the tetraploid female parent 4XASSS4 is ready to flower. Female flower buds that are ready to open the next day are identified, covered with paper cups or small paper bags that prevent bee or any other insect visit of the female flowers, and marked with any kind of material that can be easily seen the next morning. This process is best done in the afternoon. The male flowers of the diploid male parent are collected in the early morning before they are open and visited by pollinating insects. The covered female flowers of the tetraploid female parent, which have opened, are un-covered and pollinated with the collected fresh male flowers of the diploid male parent, starting as soon as the male flower sheds pollen. The pollinated female flowers are again covered after pollination to prevent bees and any other insects visit. The pollinated female flowers are also marked. Only the marked fruits are harvested for extracting triploid hybrid seed.

Bee-Pollination Method

Using the bee-pollination method, the tetraploid female parent 4XASSS4 and the diploid male parent are usually planted in a ratio of 2 rows tetraploid parent to 1 row male parent. The female tetraploid plants are pruned to 2-3 branches. All the male flower buds on the female tetraploid parent plants are removed manually, (the de-budding process), during the pollination season on a daily basis. Beehives are placed in the field for transfer of pollen by bees from the male parent to the female flowers of the female parent. Fruits set during this de-budding time are marked. Only the marked fruits are harvested for extracting hybrid triploid seed.

According to the invention, tetraploid inbreds are used as parental lines to develop new tetraploid lines. The unique and desirable traits of 4XASSS4 make it very useful as a parental line in the development of new tetraploid inbreds. 4XASSS4 can be used as either female or male parent to cross with another inbred or hybrid tetraploid to develop new tetraploid inbreds.

TABLE 5

Description of the tetraploid inbred 4XASSS4 and comparison to tetraploid 90-4265

| Characteristic: | 4XASSS4 | 90-4265 |
| --- | --- | --- |
| Fruit: | oblong | round, large |
| Area of best adaptation: | most areas | most areas |
| Emergence of anthesis: | 34 days | 36 days |
| Pollination to maturity: | 34 days | 37 days |
| Relative maturity: | 103 days | 108 days |
| Maturity category: | medium | medium |
| Ploidy: | tetraploid | tetraploid |
| Cotyledon: | flat | flat |
| Sex: | monoecious | monoecious |
| Number of Main Stems: | 5 at crown | 5 at crown |
| Number of flowers at first fruit set: | 25 staminate, 3 pistillate, 0 perfect | 25 staminate, 3 pistillate, 0 perfect |
| Stem: | round, pubescent, 9 mm diameter at second node | round, pubescent, 9 mm diameter at second node |
| Vine length: | 240 cm at late harvest | 220 cm at late harvest |
| No. internodes: | 23 at late harvest | 22 at late harvest |

TABLE 5-continued

Description of the tetraploid inbred 4XASSS4
and comparison to tetraploid 90-4265

| Characteristic: | 4XASSS4 | 90-4265 |
|---|---|---|
| Ratio cm vine length/internodes: | 10.4 | 10.0 |
| Leaf: | Lobed ovate | Lobed ovate |
| Flower at first fruit set: | staminate 4.5 cm across, pistillate 4 cm across, yellow | staminate 4.0 cm across, pistillate 3.5 cm across, yellow |
| Mature fruit size: | oval, 26 cm long, 23 cm diameter at midsection, 8.4 kg average weight, 11.1 kg maximum, smooth surface, light green rind with dark green stripes | round, 24 cm long, 24 cm diameter at midsection, 6.9 kg average weight, 8.1 kg maximum, smooth surface, solid light green rind |
| Rind: | tough, 11 mm thick blossom end, 14 mm thick sides | tough, 12 mm thick blossom end, 16 mm thick sides |
| Flesh: | crisp, fine with little fiber, dark red, 12% soluble solids of juice, no hollow heart, placental separation, or transverse crack | crisp, fine with little fiber, red, 11% soluble solids of juice, no hollow heart, placental separation, or transverse crack |
| Seed: | small, 7 mm long, 5 mm wide, 3 mm thick, index (length ÷ width × 10) is 14, 36 gm per 1000 seed, 75 seed per fruit, dark brown | small, 7 mm long, 5 mm wide, 3 mm thick, index (length ÷ width × 10) is 14, 34 gm per 1000 seed, 75 seed per fruit, dark brown |
| Anthracnose, Race 1: | Resistant | Untested |
| *Fusarium* Wilt, Race 1: | Resistant | Susceptible |

Although the foregoing invention has been described in some detail in this document, it will be obvious that changes and modification may be practiced within the scope of the invention, as limited only by the scope of the appended claims.

DEPOSIT INFORMATION

Applicants have made a deposit of at least 2500 seeds of watermelon inbred line 4XASSS4 with the American Type Culture Collection (ATCC), 10801 University Boulevard, Manassas, Va., 20110-2209 U.S.A., ATCC Deposit No: PTA-11775. This deposit of the watermelon inbred line 4XASSS4 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801-1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. Seed of tetraploid watermelon 4XASSS4, a representative sample of seed having been deposited under ATCC Accession No. PTA-11775.

2. A tetraploid watermelon plant, or parts thereof, of tetraploid watermelon 4XASSS4, a representative sample of seed of said watermelon plant having been deposited under ATCC Accession No. PTA-11775.

3. A tetraploid watermelon plant, or parts thereof, having all the physiological and morphological characteristics of the watermelon plant of claim 2.

4. Pollen of the plant of claim 2.

5. An ovule of the plant of claim 2.

6. A tetraploid watermelon plant regenerated from tissue of said watermelon plant of claim 2, wherein said watermelon plant has all the physiological and morphological characteristics of the watermelon plant of claim 2.

7. A tetraploid watermelon plant according to claim 6, wherein said tissue is selected from: (a) the group of tissue consisting of embryos, meristems, cotyledons, pollen, leaves, anthers, roots, root tips, seed, and stalks, or b) protoplasts or callus derived from one of said tissue.

8. A method of producing triploid hybrid seed, the method comprising crossing said tetraploid watermelon plant of claim 2 with a diploid parent watermelon plant.

9. A triploid hybrid watermelon seed produced by the method of claim 8.

10. A triploid hybrid watermelon plant and fruit, or parts thereof, grown from the seed of claim 9.

11. The method of claim 8, wherein the said tetraploid plant is the female parent.

12. The method of claim 8, wherein the said diploid plant is the male parent.

13. A method of developing a tetraploid watermelon line in a watermelon plant breeding program using plant breeding techniques, which include employing a watermelon plant, or its parts, as a source of plant breeding material, comprising: (a) obtaining the watermelon plant, or its parts, of claim 2 as a source of breeding material; and (b) applying plant breeding techniques.

14. A watermelon plant breeding program of claim 13, wherein said plant breeding techniques are selected from the group consisting of: recurrent selection, backcrossing, pedigree breeding, genetic marker assisted selection, and genetic transformation.

15. A tetraploid watermelon plant, or parts thereof, produced by crossing the plant of claim 2 with a different inbred tetraploid watermelon plant or a hybrid tetraploid watermelon plant.

* * * * *